United States Patent
Fukuta et al.

(10) Patent No.: US 8,377,335 B2
(45) Date of Patent: Feb. 19, 2013

(54) SOLID SCINTILLATOR, RADIATION DETECTOR, AND TOMOGRAPH

(75) Inventors: Yukihiro Fukuta, Yokohama (JP); Hiroyasu Oota, Shinagawa-Ku (JP); Tsutomu Ishii, Yokohama (JP); Yoshitaka Funayama, Yokohama (JP)

(73) Assignees: Kabushiki Kaisha Toshiba, Tokyo (JP); Toshiba Materials Co., Ltd., Yokohama-shi (JP)

( * ) Notice: Subject to any disclaimer, the term of this patent is extended or adjusted under 35 U.S.C. 154(b) by 0 days.

(21) Appl. No.: 13/202,825

(22) PCT Filed: Feb. 22, 2010

(86) PCT No.: PCT/JP2010/052625
§ 371 (c)(1),
(2), (4) Date: Aug. 31, 2011

(87) PCT Pub. No.: WO2010/095737
PCT Pub. Date: Aug. 26, 2010

(65) Prior Publication Data
US 2011/0303873 A1  Dec. 15, 2011

(30) Foreign Application Priority Data
Feb. 23, 2009 (JP) .................... 2009-039040

(51) Int. Cl.
*C09K 11/61* (2006.01)
*C09K 11/08* (2006.01)
(52) U.S. Cl. ............... 252/301.4 H; 252/301.4 F
(58) Field of Classification Search ........... 252/301.17, 252/301.4 R, 301.4 F, 301.4 H; 501/126, 501/151, 152; 250/370.11
See application file for complete search history.

(56) References Cited

U.S. PATENT DOCUMENTS

| | | | | |
|---|---|---|---|---|
| 6,479,420 B2 * | 11/2002 | Nakamura | ............ | 501/152 |
| 6,538,371 B1 | 3/2003 | Duggal et al. | | |
| 7,252,787 B2 * | 8/2007 | Hancu et al. | ............ | 252/301.4 R |
| 8,133,461 B2 * | 3/2012 | Tao et al. | ............ | 423/263 |
| 2002/0013215 A1 | 1/2002 | Nakamura | | |
| 2004/0066883 A1 | 4/2004 | Kanai et al. | | |
| 2005/0156496 A1 * | 7/2005 | Takashima et al. | ............ | 313/237 |
| 2008/0138268 A1 * | 6/2008 | Tao et al. | ............ | 423/263 |

FOREIGN PATENT DOCUMENTS

| | | |
|---|---|---|
| JP | 2001 4753 | 1/2001 |
| JP | 2001 181043 | 7/2001 |
| JP | 2001 183463 | 7/2001 |
| JP | 2001 294853 | 10/2001 |
| JP | 2001 320094 | 11/2001 |
| JP | 2001 348273 | 12/2001 |
| JP | 2002 189080 | 7/2002 |
| JP | 2009 227794 | 10/2009 |

OTHER PUBLICATIONS

International Preliminary Report on Patentability issued Sep. 13, 2011 in PCT/JP10/052625 filed Feb. 22, 2010.
International Search Report Issued May 18, 2010 in PCT/JP10/052625 filed Feb. 22, 2010.

* cited by examiner

*Primary Examiner* — Emily Le
*Assistant Examiner* — Lynne Edmondson
(74) *Attorney, Agent, or Firm* — Oblon, Spivak, McClelland, Maier & Neustadt, L.L.P.

(57) ABSTRACT

A solid scintillator having short afterglow and high output, containing a polycrystal containing a crystal of a Gd garnet structure oxide having a composition ratio of formula (1):

$$(M_{1-x-y}Gd_xQ_y)_3J_5O_{12} \tag{1}$$

where M is at least one element of La and Tb, Q is at least one element of Ce and Pr, J is at least one element selected from Al, Ga, and In, x and y satisfy the relations $0.5 \leq x < 1$, and $0.000001 \leq y \leq 0.2$, and further containing Si and fluorine, where the solid scintillator contains 1 ppm by mass to 1000 ppm by mass of the Si with respect to the Gd garnet structure oxide, and 1 ppm by mass to 100 ppm by mass of the fluorine with respect to the Gd garnet structure oxide. In addition a radiation detector and a tomograph employing the solid scintillator.

20 Claims, No Drawings

SOLID SCINTILLATOR, RADIATION DETECTOR, AND TOMOGRAPH

TECHNICAL FIELD

The present invention relates to a technique for converting radiation such as X-rays, to visible light and the like, and particularly to a solid scintillator, and a radiation detector and a tomograph using this solid scintillator.

BACKGROUND ART

In fields of medical diagnosis, industrial inspection, security and the like, inspection using a radiation inspection apparatus such as a tomograph (X-ray CT apparatus), is performed. The X-ray CT apparatus usually contains an X-ray tube (X-ray source) for irradiating fan beam X-rays, a fan-shaped X-ray beam, an X-ray detector opposed to the X-ray tube and having many X-ray detection elements, and an image reconstruction apparatus for reconstructing an image based on data send from the X-ray detector. An object is placed between the X-ray tube and the X-ray detector, and a cross-sectional plane is imaged by irradiation with fan beam X-rays.

The X-ray CT apparatus repeatedly performs an operation of irradiating fan beam X-rays and collecting X-ray absorption data, with changing an irradiation angle to the cross-sectional plane in turn, for example, by 1 degree at a time. Then, the X-ray CT apparatus analyzes the obtained data, calculates an X-ray absorptance of the object on the cross-sectional plane, and constructs an image of the cross-sectional plane according to this absorptance by a computer.

A solid scintillator for radiating visible light and the like by stimulation of X-rays is used as the X-ray detector of the X-ray CT apparatus. The solid scintillator means a scintillator containing ceramic or a single crystal, among scintillators.

When the solid scintillator is used as the X-ray detector of the X-ray CT apparatus, it is preferable that the detection elements are miniaturized, and it is easy to increase the number of channels, and therefore, higher resolution is possible.

Conventionally, as a solid scintillator used for a radiation detector such as an X-ray detector, for example, single crystals, such as cadmium tungstate ($CdWO_4$), sodium iodide (NaI), and cesium iodide (CsI), barium fluoride chloride:europium (BaFCl:Eu), lanthanum oxybromide:terbium (LaOBr:Tb), cesium iodide:thallium (CsI:Tl), calcium tungstate ($CaWO_4$), cadmium tungstate ($CdWO_4$), gadolinium oxysulfide:praseodymium ($Gd_2O_2S$:Pr) disclosed in Japanese Patent Laid-Open No. 58-204088 (Patent Document 1), and the like have been known.

Among these solid scintillators, rare earth oxysulfide ceramics such as $Gd_2O_2S$:Pr, have a large X-ray absorption coefficient to allow miniaturization of the solid scintillator, and provide a short afterglow time of light emission and therefore have high time resolution. Therefore, rare earth oxysulfide ceramics is preferable for a scintillator for X-ray detection and a rare earth oxysulfide ceramics scintillator is widely put to practical use.

However, in recent years, a scintillator that has short afterglow, can perform high speed scanning, and has high light output has been desired so as to reduce an X-ray exposure amount of a patient.

Conventionally, as solid scintillators having short afterglow, garnet structure oxides using $Ce^{3+}$ of rare earth as a light-emitting ion have been known.

For example, Japanese Patent Laid-Open No. 2005-126718 (Patent Document 2) proposes garnet structure oxides such as $(Tb_{1-y}, Ce_y)_a(Al, Ga, In)_zO_{12}$ and $(Lu_{1-y}, Ce_y)_a(Al, Ga, In)_zO_{12}$, and International Publication No. WO 99/33934 (Patent Document 3) proposes a garnet structure oxide such as $(Gd_{1-x}, Ce_x)_3Al_{5-y}Ga_yO_{12}$.

As a method for manufacturing these solid scintillators, a method for making a sintered body by a hot pressing (uniaxial pressing) method, an HIP method (hot isostatic pressing method), or a vacuum sintering method is used.

CITATION LIST

Patent Literature

Patent Document 1: Japanese Patent Laid-Open No. 58-204088

Patent Document 2: Japanese Patent Laid-Open No. 2005-126718

Patent Document 3: International Publication No. WO 99/33934

Patent Document 4: Japanese Patent Laid-Open No. 2008-174432

SUMMARY OF INVENTION

Problems to be Solved by the Invention

In order that a solid scintillator which comprises a garnet structure oxide containing Ce and has short afterglow, has higher output, it is necessary that the garnet structure oxide has a dense sintered body having high density so as to have a structure with less X-ray scattering.

However, when the garnet structure oxide is a Gd garnet structure oxide, a problem is that it is difficult to obtain a sintered body of the Gd garnet structure oxide having high density, only by reviewing a sintering program with the hot pressing (uniaxial pressing) method or the vacuum sintering method.

The present invention has been made in view of the above circumstances. It is an object of the present invention to provide a solid scintillator having short afterglow and high output, and a radiation detector and a tomograph using the solid scintillator.

Means for Solving the Problems

The present invention has been completed by finding the following. When a raw material powder containing at least one of Ce and Pr and the like is fired with a fluoride as a reaction promoter, a powder of a single crystal of a garnet structure oxide is obtained. Further, in the case silica is added as a sintering aid when a raw material powder for a solid scintillator containing a Gd garnet structure oxide which is a structure of the single crystal is sintered to make a solid scintillator, the Gd garnet structure oxide contains Si to provide a sintered body having high density, and thus, a solid scintillator having short afterglow and high output can be obtained.

A solid scintillator according to the present invention solves the above problem and is a solid scintillator comprising a polycrystal containing a crystal of a Gd garnet structure oxide having a composition ratio represented by the following formula (1):

[Formula 1]

$$(M_{1-x-y}Gd_xQ_y)_3J_5O_{12} \qquad (1)$$

wherein M is at least one element of La and Tb, Q is at least one element of Ce and Pr, J is at least one element selected from Al, Ga, and In, x and y satisfy relations 0.5≦x<1, and 0.000001≦y≦0.2, and further containing Si and fluorine, wherein the solid scintillator contains 1 ppm by mass to 1000 ppm by mass of the Si with respect to the Gd garnet structure oxide, and 1 ppm by mass to 100 ppm by mass of the fluorine with respect to the Gd garnet structure oxide.

In addition, a radiation detector according to the present invention solves the above problem and uses the above solid scintillator.

Further, a tomograph according to the present invention solves the above problem and uses the above radiation detector.

Advantages of the Invention

The solid scintillator according to the present invention provides a solid scintillator having short afterglow and high output.

In addition, the radiation detector according to the present invention provides a radiation detector that can perform high speed scanning and has high output.

Further, the tomograph according to the present invention provides a tomograph that can perform high speed scanning and has high output.

DESCRIPTION OF EMBODIMENTS

[Solid Scintillator]

A solid scintillator according to the present invention comprises a polycrystal containing a crystal of a Gd garnet structure oxide having a particular composition ratio, and further containing Si and fluorine, and the solid scintillator has a bulky form. The crystal of the Gd garnet structure oxide in the solid scintillator is a single crystal, and the solid scintillator is a polycrystal containing a plurality of the single crystals.

In the solid scintillator, many of the Si is dissolved in particles of single crystal grains of the Gd garnet structure oxide having a particular composition ratio, and a remainder of the Si is present in grain boundaries between the above single crystal grains.

In addition, in the solid scintillator, the fluorine is mainly present in grain boundaries between the single crystal grains constituting the polycrystal. The fluorine may be present in the single crystal grains.

(Crystal of Gd Garnet Structure Oxide)

The crystal of the Gd garnet structure oxide constituting the solid scintillator has a composition ratio represented by the following formula (1). In addition, usually, the crystal of the Gd garnet structure oxide also contains a Si component.

[Formula 2]

$(M_{1-x-y}Gd_xQ_y)_3J_5O_{12}$ (1)

In the formula (1), M is at least one element of La and Tb, Q is at least one element of Ce and Pr, and J is at least one element selected from Al, Ga, and In.

In the formula (1), x is 0.5≦x<1. When x is 0.5≦x<1, that is, when a content of Gd in a total amount of M, Gd, and Q is 50 mol % or more and less than 100 mol %, an X-ray absorption coefficient and light emission efficiency are high, which is preferred.

If x is less than 0.5, that is, if the content of Gd in the total mount of M, Gd, and Q is less than 50 mol %, X-rays cannot be sufficiently absorbed in the solid scintillator, and therefore, light emission output may decrease.

In the formula (1), y is 0.000001≦y≦0.2, preferably 0.001≦y≦0.1.

In the solid scintillator according to the present invention, Q, that is, at least one element of Ce and Pr, is an activator for increasing a light emission efficiency of the Gd garnet structure oxide represented by the formula (1). When y is 0.000001≦y≦0.2, that is, when a content of Q in the total amount of M, Gd, and Q is 0.0001 mol % or more and 20 mol % or less, the light emission efficiency is high, which is preferred.

If y is less than 0.000001, that is, if the content of Q in the total amount of M, Gd, and Q is less than 0.0001 mol %, the light emission efficiency may decrease due to an insufficient content of Q contributing to light emission.

If y is more than 0.2, that is, if the content of Q in the total amount of M, Gd, and Q is more than 20 mol %, a material is colored, and therefore, transparency is low, and sufficient light emission output may not be obtained.

(Fluorine in Solid Scintillator)

The fluorine in the solid scintillator is a remainder of a fluorine component included in a phosphor powder (a powder for manufacturing a solid scintillator) obtained by firing a reaction promoter-containing powder that is a mixture of raw material powders such as $Gd_2O_3$, $CeO_2$, and $Al_2O_3$, and a fluoride such as $AlF_3$, that is a reaction promoter. The solid scintillator is obtained by sintering a mixed powder containing the phosphor powder. In sintering, the fluorine component included in the phosphor powder changes into the fluorine, and the fluorine remains in the solid scintillator. Here, the fluorine in the solid scintillator is used in a sense including not only a simple substance of fluorine, but also a fluoride.

In the solid scintillator according to the present invention, the fluorine is mainly present as a rare earth fluoride, though it is also present as a simple substance of fluorine. Presence of the rare earth fluoride in the solid scintillator can be detected by EPMA, for example.

In the present invention, a content of fluorine means a mass of a simple substance of fluorine equivalent to the fluorine. For example, when fluorine is detected as both a fluorine compound such as a fluoride, and a simple substance of fluorine, the content of fluorine is calculated as a total value of a fluorine amount of the simple substance of fluorine, and a fluorine amount of a simple substance of fluorine equivalent to the fluorine compound.

The solid scintillator contains 1 ppm by mass to 100 ppm by mass, preferably 4 ppm by mass to 87 ppm by mass, and further preferably 4 ppm by mass to 47 ppm by mass, of fluorine with respect to the Gd garnet structure oxide represented by the formula (1) in the solid scintillator.

When the content of fluorine in the solid scintillator is 1 ppm by mass to 100 ppm by mass with respect to the garnet structure oxide, the solid scintillator is a polycrystal containing only a Gd garnet structure oxide crystal, that is, a single phase of a Gd garnet structure oxide crystal, and therefore, the solid scintillator tends to have short afterglow and high output.

In addition, when the content of fluorine is 1 ppm by mass to 100 ppm by mass, the fluorine, that is, a simple substance of fluorine, a fluoride and the like, which is present in grain boundaries of the Gd garnet structure oxide crystals strengthens bonding force between Gd garnet structure oxide crystal grains. Therefore, detachment of crystal grains is less likely to occur on a cut surface of a solid scintillator cut from a sintered body obtained as an ingot of a polycrystal containing only a Gd garnet structure oxide crystal, and a surface state of the cut surface of the solid scintillator is good, and polishing of the cut surface is not required. Therefore, a lower cost of the solid scintillator is possible.

Further, when the content of fluorine is 1 ppm by mass to 100 ppm by mass, firing temperature in firing the reaction promoter-containing powder so as to provide the phosphor powder that is a sintering raw material for the solid scintillator can be a temperature as low as 1100° C. to 1400° C.

A reason why a temperature as low as 1100° C. to 1400° C. is preferable for the firing temperature in firing for the phosphor powder is as follows.

In a case where only the raw material powders are fired, without using the reaction promoter, so as to provide the phosphor powder containing the Gd garnet structure oxide represented by the formula (1), if the firing temperature is more than 1400° C., lumps are formed in the phosphor powder after the firing, which may adversely affect a subsequent scintillator making step. In addition, if the firing temperature is 1100° C. or less, a firing reaction may not occur sufficiently.

On the other hand, when a predetermined amount of a fluorine component that is the reaction promoter is mixed, in addition to the raw material powders in firing for the phosphor powder, a firing reaction occurs sufficiently even at 1400° C. or less, which is a firing temperature at which substantially lumps are not formed. Therefore, a good phosphor powder having a composition represented by the formula (1), containing a predetermined amount of the fluorine component, and being in a powder state including no lumps is obtained.

A content of fluorine of the good phosphor powder is an amount similar to a fluorine amount in the solid scintillator. In other words, the phosphor powder contains 1 ppm by mass to 100 ppm by mass, preferably 4 ppm by mass to 87 ppm by mass, and further preferably 4 ppm by mass to 47 ppm by mass, of fluorine with respect to the Gd garnet structure oxide represented by the formula (1) in the phosphor powder.

When the phosphor powder is sintered with a sintering aid, a solid scintillator in which a content of fluorine is 1 ppm by mass to 100 ppm by mass with respect to the Gd garnet structure oxide represented by the formula (1) is obtained.

In this manner, the solid scintillator in which the content of fluorine is 1 ppm by mass to 100 ppm by mass with respect to the Gd garnet structure oxide represented by the formula (1) is a solid scintillator obtained by sintering a phosphor powder that is obtained by firing at a low firing temperature of 1100° C. to 1400° C. and is in a powder state containing no lumps and has good properties. Therefore, the solid scintillator has excellent characteristics such as light emission efficiency, which is preferred.

On the other hand, if the content of fluorine in the solid scintillator is less than 1 ppm by mass with respect to the Gd garnet structure oxide, the oxide crystal of the solid scintillator is not a single phase of the Gd garnet structure, and a light emission output of the solid scintillator may decrease. In other words, if an amount of the fluoride as the reaction promoter mixed in the reaction promoter-containing powder is small, the oxide crystal of the solid scintillator tends to form a crystal structure other than the garnet structure, for example, a perovskite structure. If the oxide crystal of the solid scintillator has a crystal structure other than the garnet structure in this manner, the light emission output of the solid scintillator tends to decrease.

In addition, if the content of fluorine in the solid scintillator is more than 100 ppm by mass with respect to the Gd garnet structure oxide, an excessive amount of fluorine remains as an impurity in crystal grains or grain boundaries of the Gd garnet structure oxide of the solid scintillator. The remainder of the fluorine in crystal grains or grain boundaries causes light scattering, and the light emission output of the solid scintillator may decrease.

(Si in Solid Scintillator)

The solid scintillator according to the present invention is obtained by cutting a sintered body containing a polycrystal of a Gd garnet structure oxide single crystal having a composition ratio represented by the formula (1). The sintered body is obtained by first firing a mixture of raw material powders and a fluoride that is a reaction promoter so as to produce a Gd garnet structure oxide single crystal powder (phosphor powder) having the composition ratio represented by the formula (1), and then sintering this phosphor powder with silica that is a sintering aid.

Si in the solid scintillator is a remainder of Si derived from the silica ($SiO_2$) added as the sintering aid in particles of single crystal grains of the Gd garnet structure oxide in the solid scintillator after the sintering.

The solid scintillator contains 1 ppm by mass to 1000 ppm by mass, preferably 10 ppm by mass to 100 ppm by mass, of Si with respect to the Gd garnet structure oxide represented by the formula (1).

If the content of Si in the solid scintillator is less than 1 ppm by mass with respect to the Gd garnet structure oxide, the Gd garnet structure oxide may not be sufficiently densified.

In addition, if the content of Si in the solid scintillator is more than 1000 ppm by mass with respect to the Gd garnet structure oxide, excessive Si becomes an impurity that affects light emission characteristics, and light scattering occurs. Therefore, light emission output of the solid scintillator may decrease.

[Method for Manufacturing Solid Scintillator]

The solid scintillator according to the present invention can be made, for example, by a manufacturing method having a reaction promoter-containing powder preparing step, a firing step, a mixed powder preparing step, and a sintering step.

(Reaction Promoter-Containing Powder Preparing Step)

The reaction promoter-containing powder preparing step is a step of mixing raw material powders that are raw materials for making a Gd garnet structure oxide single crystal having a composition ratio represented by the above formula (1), and a fluoride that is a reaction promoter, so as to obtain a reaction promoter-containing powder.

<Raw Material Powders>

Examples of the raw material powders used in the present invention include $Tb_4O_7$, $La_2O_3$, $Gd_2O_3$, $Al_2O_3$, $Ga_2O_3$, and $CeO_2$ powders.

<Reaction Promoter>

Examples of the fluoride as the reaction promoter include rare earth fluorides such as $GdF_3$ and $TbF_3$; fluorides of Group IIIB such as $AlF_3$ and $GaF_3$; and fluorides of Group IIA such as $BaF_2$. Among these, the rare earth fluoride or the fluoride of Group IIIB is preferred because it can become a substance constituting a matrix of the Gd garnet structure oxide, and therefore, it does not become an impurity even if it remains in the solid scintillator.

The fluoride used in the present invention is a reaction promoter that, in firing the reaction promoter-containing powder to provide a phosphor powder that is of oxide single crystal particles in the following firing step, makes a crystal of the phosphor powder have a garnet structure.

Specifically, the fluoride is a reaction promoter that promotes a garnet structure of the crystal of the phosphor powder by occurrence of a solid phase-liquid phase reaction. The fluoride melts on surfaces of particles of the phosphor powder and between the particles during firing the reaction promoter-containing powder to provide the phosphor powder.

A reason why the fluoride is used as the reaction promoter is as follows.

In order that the reaction promoter causes a solid phase-liquid phase reaction on the surfaces of the particles of the phosphor powder and between the particles during firing in the following firing step, it is required that the reaction promoter has such a low melting point that it melts on the surfaces of the particles of the phosphor powder during firing, and such a high boiling point that it does not volatilize before firing for the phosphor powder is completed.

In addition, the phosphor powder contains single crystal particles of a Gd-containing garnet structure ($M_3N_5O_{12}$) oxide having a composition ratio represented by the formula (1), and the single crystal particles further contains a fluorine component derived from the reaction promoter. And a problem of the phosphor powder is that if firing temperature in firing for the phosphor powder is more than 1400° C., lumps are formed in the powder after firing. Another problem of the phosphor powder is that if the firing temperature is more than 1400° C., a crystal structure of single crystal particles of the Gd garnet structure oxide may be a perovskite structure ($M_1N_1O_3$) or a monoclinic structure ($M_4N_2O_9$), other than the garnet structure. Therefore, it is required of the reaction promoter included in the reaction promoter-containing powder to be able to make the single crystal particles of the oxide of the phosphor powder have a garnet structure under a firing condition of 1400° C. or less.

Further, the phosphor powder takes the form of a powder, and therefore, the reaction promoter is required of having a characteristic of which the Gd garnet structure oxide obtained by firing the reaction promoter-containing powder containing the reaction promoter does not become a glassy form.

The solid scintillator according to the present invention is made by sintering the phosphor powder. Therefore, if the Gd garnet structure oxide obtained by firing the reaction promoter-containing powder is glassy, a phosphor powder having a uniform size cannot be obtained, a solid scintillator having high light emission output cannot be obtained.

In other words, if the Gd garnet structure oxide obtained by firing the reaction promoter-containing powder is glassy, it is difficult to sinter the glassy Gd garnet structure oxide to obtain a solid scintillator, and it is difficult to obtain a phosphor powder having a uniform size even if the glassy Gd garnet structure oxide is subjected to treatment such as pulverization. As a result, it is difficult to obtain a solid scintillator having high light emission output.

Therefore, the above characteristics, that is, characteristics of having such a low melting point as melting on the surfaces of the particles of the phosphor powder during firing in which the reaction promoter-containing powder is fired to provide the phosphor powder, having such a high boiling point as not volatilizing before completion of firing for the phosphor powder, and being able to perform firing for the phosphor powder at 1400° C. or less without becoming glassy, are required of the reaction promoter used in the present invention. The fluoride used in the present invention satisfies these characteristics.

It is preferable that the reaction promoter-containing powder contains a mixture of an amount of raw material powders prepared to make 1 mole of the garnet structure oxide having the composition ratio represented by the above formula (1), and a fluoride equivalent to $10 \times 10^{-6}$ moles to $500 \times 10^{-6}$ moles of fluorine. Because a fluorine content of a phosphor powder obtained by firing the reaction promoter-containing powder, and a fluorine content of a sintered body and a solid scintillator obtained by sintering the phosphor powder with a sintering aid tend to be in a preferred range.

In addition, in the reaction promoter-containing powder that is a firing raw material for a phosphor, an amount of the reaction promoter mixed is usually equivalent to 10 ppm by mass to 500 ppm by mass, preferably 10 ppm by mass to 400 ppm by mass, and further preferably 100 ppm by mass to 400 ppm by mass, of fluorine, with respect to a mass of a Gd garnet structure oxide phosphor at a theoretical yield obtained after firing.

When the reaction promoter is mixed so that a fluorine amount in the reaction promoter, based on a mass of the above Gd garnet structure oxide in the phosphor powder at a theoretical yield, is 10 ppm by mass to 500 ppm by mass, the phosphor powder obtained by firing the reaction promoter-containing powder, and the sintered body and the solid scintillator obtained by sintering the phosphor powder have a polycrystal containing only a garnet structure oxide crystal, that is, a single phase of a Gd garnet structure oxide crystal, and therefore, the solid scintillator tends to have short afterglow and high output.

In addition, when the reaction promoter is mixed so that an amount of a fluorine compound mixed in the reaction promoter-containing powder is equivalent to 10 ppm by mass to 500 ppm by mass of fluorine, bonding force between Gd garnet structure oxide crystal grains is strong due to fluorine, that is, a simple substance of fluorine, a fluoride and the like, being present in grain boundaries of the Gd garnet structure oxide crystals, in the phosphor powder obtained by firing the reaction promoter-containing powder, and the sintered body and the solid scintillator obtained by sintering the phosphor powder. Therefore, detachment of crystal grains is less likely to occur on a cut surface of the solid scintillator cut from the sintered body obtained as an ingot of a polycrystal containing only a Gd garnet structure oxide crystal. Thus, a surface state of the cut surface of the solid scintillator is good, and no polishing is required. Accordingly, a lower cost of the solid scintillator is possible.

Further, when the reaction promoter is mixed so that the amount of the fluorine compound mixed in the reaction promoter-containing powder is equivalent to 10 ppm by mass to 500 ppm by mass of fluorine, firing temperature in firing the reaction promoter-containing powder to provide the phosphor powder can be a temperature as low as about 1100° C. to 1400° C.

Therefore, there is no problem of formation of lumps in the phosphor powder in firing for the phosphor powder, and a solid scintillator having predetermined characteristics can be made, which is preferred.

A reason why a temperature as low as 1100° C. to 1400° C. is preferable for the firing temperature in firing for the phosphor powder is as follows.

In a case where only the raw material powders are fired, without using the reaction promoter, so as to provide the phosphor powder containing the Gd garnet structure oxide represented by the formula (1), if the firing temperature is more than 1400° C., lumps are formed in the phosphor powder after the firing, which may adversely affect a subsequent scintillator making step. In addition, if the firing temperature is 1100° C. or less, a firing reaction may not occur sufficiently.

On the other hand, when a predetermined amount of a fluorine component that is the reaction promoter is mixed in addition to the raw material powders in firing for the phosphor powder, a firing reaction is promoted sufficiently even at 1400° C. or less, which is a firing temperature at which substantially lumps are not formed. Therefore, a phosphor powder having a composition represented by the formula (1), containing a predetermined amount of the fluorine component, being in a powder state containing no lumps, and having good light emission characteristics is obtained.

In this manner, when the reaction promoter is mixed so that the amount of the fluorine compound mixed in the reaction promoter-containing powder is equivalent to 10 ppm by mass to 500 ppm by mass of fluorine, an obtained phosphor powder is a good phosphor powder in a powder state containing no lumps, which is preferred.

On the other hand, if the reaction promoter is mixed so that the amount of the fluorine compound mixed in the reaction promoter-containing powder is equivalent to less than 10 ppm by mass of fluorine, the oxide crystal of the phosphor powder obtained by firing the reaction promoter-containing powder and the sintered body and the solid scintillator obtained by sintering the phosphor powder is not a single phase of the Gd garnet structure, and a light emission output of the solid scintillator may decrease. In other words, if a content of fluorine in the phosphor powder is low, the oxide crystal of the sintered body and the solid scintillator has a crystal structure other than the garnet structure, for example, a perovskite structure. Therefore, a light emission output of the sintered body and the solid scintillator obtained by cutting the sintered body tends to decrease.

In addition, if the reaction promoter is mixed so that the fluorine amount in the reaction promoter, based on the mass of the above Gd garnet structure oxide in the phosphor powder at the theoretical yield, is more than 500 ppm by mass, an excessive amount of fluorine may remain as an impurity in crystal grains or grain boundaries of the garnet structure oxide of the phosphor powder obtained by firing the reaction promoter-containing powder and the sintered body and the solid scintillator obtained by sintering the phosphor powder. And the excessive amount of fluorine as an impurity may cause light scattering, and the light emission output of the solid scintillator may decrease.

The reaction promoter-containing powder usually has a maximum particle diameter of 200 mesh to 50 mesh. Here, X mesh means a particle diameter passing through a sieve having a mesh having (1/X) inch sides.

(Firing Step)

The firing step is a step of firing the reaction promoter-containing powder to obtain a phosphor powder.

For example, air is used as a firing atmosphere. Firing temperature is 1100° C. to 1400° C., preferably 1200° C. to 1400° C. Firing time is usually 2 hours to 6 hours.

<Phosphor Powder>

The phosphor powder (the powder for manufacturing a solid scintillator) obtained in this step is different from the solid scintillator according to the present invention described above in that the solid scintillator is a bulky polycrystal, whereas the phosphor powder is a powder of single crystal particles, that the content of fluorine is different, and that the phosphor powder does not contain Si, and other respects are the same. Therefore, explanation is omitted or simplified for the same respects between the phosphor powder according to the present invention and the solid scintillator according to the present invention.

The phosphor powder contains a single crystal composed of a Gd garnet structure oxide having a composition ratio represented by the above formula (1). The Gd garnet structure oxide contains fluorine. And the phosphor powder has a powdery form.

The crystal of the Gd garnet structure oxide having the composition ratio represented by the above formula (1) in the phosphor powder is similar to that of the solid scintillator, and therefore, explanation is omitted.

Primary particles of the phosphor powder are single crystals, and the primary particles tend to aggregate to form secondary particles. In the secondary particles, the fluorine is usually present in grain boundaries between the primary particles. In the secondary particles, a fluorine compound present in the grain boundaries between the primary particles is, for example, a rare earth fluoride.

The fluorine in the phosphor powder is a remainder of a fluorine component derived from a fluoride that is mixed as the reaction promoter in the reaction promoter-containing powder in firing the reaction promoter-containing powder to provide the phosphor powder, after the firing.

A fluorine amount in the phosphor powder is similar to the fluorine amount in the solid scintillator. In other words, the phosphor powder contains 1 ppm by mass to 100 ppm by mass, preferably 4 ppm by mass to 87 ppm by mass, and further preferably 4 ppm by mass to 47 ppm by mass, of fluorine with respect to the Gd garnet structure oxide represented by the formula (1) in the phosphor powder.

In the present invention, the fluorine amount means a mass of a simple substance of fluorine equivalent to the fluorine, as in the fluorine amount in the solid scintillator.

When the content of fluorine in the phosphor powder is 1 ppm by mass to 100 ppm by mass with respect to the Gd garnet structure oxide, the sintered body and the solid scintillator obtained by sintering the phosphor powder is a polycrystal containing only a garnet structure oxide crystal, that is, a single phase of a Gd garnet structure oxide crystal. Therefore, the solid scintillator tends to have short afterglow and high output.

In addition, when the content of fluorine in the phosphor powder is 1 ppm by mass to 100 ppm by mass, bonding force between Gd garnet structure oxide crystal grains in the sintered body and the solid scintillator obtained by sintering the phosphor powder is strong due to fluorine, which is a simple substance of fluorine, a fluoride, and the like, and is present in grain boundaries of the Gd garnet structure oxide crystals. Therefore, detachment of crystal grains is less likely to occur on a cut surface of the solid scintillator cut from the sintered body obtained as an ingot of a polycrystal containing only a Gd garnet structure oxide crystal, and a surface state of the cut surface of the solid scintillator is good, and polishing is not required. Therefore, a lower cost of the solid scintillator is possible.

On the other hand, if the content of fluorine in the phosphor powder is less than 1 ppm by mass with respect to the Gd garnet structure oxide, the oxide crystal of the phosphor powder and the sintered body and the solid scintillator obtained by sintering the phosphor powder does not become a single phase of the Gd garnet structure, and the light emission output of the solid scintillator may decrease. In other words, if the content of fluorine in the phosphor powder is low, the oxide crystal of the sintered body and the solid scintillator has a crystal structure other than the garnet structure, for example, a perovskite structure, and the light emission output of the sintered body and the solid scintillator obtained by cutting the sintered body tends to decrease.

In addition, if the content of fluorine in the phosphor powder is more than 100 ppm by mass with respect to the Gd garnet structure oxide, an excessive amount of fluorine remains as an impurity in crystal grains or grain boundaries of the garnet structure oxide of the sintered body and the solid scintillator obtained by sintering the phosphor powder. The excessive amount of fluorine as an impurity causes light scattering, and the light emission output of the solid scintillator may decrease.

It is preferred that the phosphor powder usually has an average particle diameter $D_{50}$ of 1 µm to 10 µm. This average particle diameter $D_{50}$ is a value measured for the entire phosphor powder containing primary particles and secondary particles.

(Mixed Powder Preparing Step)

The mixed powder preparing step is a step of mixing the phosphor powder and silica that is a sintering aid to obtain a mixed powder.

<Sintering Aid>

Silica ($SiO_2$) and the like is used as the sintering aid. The silica promotes densification of location of single crystal grains of the Gd garnet structure oxide in sintering the phosphor powder in the mixed powder.

In other words, in sintering the phosphor powder to make a sintered body containing a polycrystal of a Gd garnet structure oxide crystal having a composition ratio represented by the above formula (1), the silica uniforms growth of the single crystal grains of the Gd garnet structure oxide of the phosphor powder to suppress local enlargement of the single crystal grains and reduce pores remaining in the grain boundaries, thereby densifying single crystal grains of the sintered body.

The solid scintillator is obtained by cutting the sintered body as it is, and heat-treating the cut sintered body in a heat treatment step and the like, as required. The solid scintillator is obtained by cutting and the like of the sintered body, and therefore, single crystal grains in the solid scintillator are densified as in the sintered body.

Part of the silica added as the sintering aid in sintering the phosphor powder remains in particles of the single crystal grains of the Gd garnet structure oxide in the sintered body after the sintering and the solid scintillator. However, an amount of the remaining silica is at a level that does not adversely affect optical characteristics of the solid scintillator and therefore is not a problem.

Therefore, the silica is preferred as the sintering aid for sintering the phosphor powder to make a sintered body and a solid scintillator containing a polycrystal of a Gd garnet structure oxide crystal having a composition ratio represented by the above formula (1).

The silica is mixed so that a Si equivalent amount with respect to the Gd garnet structure oxide having the composition ratio represented by the above formula (1) in the phosphor powder is 1 ppm by mass to 1000 ppm by mass, preferably 10 ppm by mass to 100 ppm by mass.

If a mixed amount of Si equivalent to the silica, with respect to the Gd garnet structure oxide of the phosphor powder, is less than 1 ppm by mass, the Gd garnet structure oxide may not be sufficiently densified.

In addition, if the mixed amount of Si equivalent to the silica, with respect to the Gd garnet structure oxide of the phosphor powder, is more than 1000 ppm by mass, excessive Si remains in an obtained solid scintillator, and this Si becomes an impurity that affects light emission characteristics, light scattering occurs, and the light emission output of the solid scintillator may decrease.

A Si component of the silica mixed as the sintering aid in the mixed powder diffuses and is taken in an interior part of bulk consisting of the sintered body, specifically, the particles of the single crystal grains of the Gd garnet structure oxide having the composition ratio represented by the above formula (1), in the following sintering step. Therefore, the Si component mixed as the sintering aid does not disappear and remains in an almost unchanged amount in the sintered body obtained in the sintering step and the solid scintillator made from the sintered body.

Therefore, the sintered body and the solid scintillator obtained by sintering the mixed powder contains 1 ppm by mass to 1000 ppm by mass, preferably 10 ppm by mass to 100 ppm by mass, of Si with respect to the Gd garnet structure oxide represented by the formula (1).

(Sintering Step)

The sintering step is a step of sintering the mixed powder to obtain a sintered body comprising a polycrystal containing a Gd garnet structure oxide crystal having a composition ratio represented by the above formula (1), and the polycrystal further contains Si and fluorine.

For example, a hot pressing method, an HIP method (hot isostatic pressing method), a vacuum sintering method, and the like are used as a sintering method for making the sintered body from the phosphor powder. For sintering conditions, usually, temperature is 1400° C. to 1700° C., and treatment time is 1 hour to 10 hours.

In heating and pressing treatment by the hot pressing method, it is preferred to at least replace an atmosphere in a treatment chamber of a hot pressing apparatus by an inert gas, such as an argon gas.

The sintered body can also be used as the solid scintillator as it is, but, usually, the sintered body cut into a predetermined shape and size is used as the solid scintillator. In addition, the cut sintered body further subjected to a heat treatment step and the like, as required, can also be used as the solid scintillator.

(Heat Treatment Step)

The heat treatment step performed, as required, after the sintering step is a step of heat-treating the sintered body after the cutting so as to obtain a solid scintillator comprising a polycrystal containing a Gd garnet structure oxide crystal having a composition ratio represented by the above formula (1), and the polycrystal further contains Si and fluorine.

When the sintered body after the cutting is subjected to the heat treatment step, a size of crystal grains of the sintered body is uniform, and arrangement of the crystal grains is aligned, and in addition, strain and the like occurring during cutting processing are removed, then variations in the light emission output of the solid scintillator are small, which are preferred.

For example, an electric furnace is used as a heat treatment apparatus.

For example, air is used as a heat treatment atmosphere. Heat treatment temperature is 1100° C. to 1400° C., preferably 1250° C. to 1350° C. Heat treatment time is usually 2 hours to 6 hours.

The solid scintillator according to the present invention provides a solid scintillator having short afterglow and high output.

[Radiation Detector]

A radiation detector according to the present invention uses the solid scintillator according to the present invention described above, for example, as an X-ray detection element of an X-ray detector.

The radiation detector according to the present invention can be configured to comprise, for example, the above solid scintillator, and a photodiode for converting light radiated from the solid scintillator to electric energy.

The radiation detector according to the present invention uses a solid scintillator having short afterglow and high output and therefore provides a radiation detector that can perform high speed scanning and has high output.

[Tomograph]

A tomograph according to the present invention uses the solid scintillator according to the present invention described above as an X-ray detection element of an X-ray detector.

The tomograph according to the present invention can be configured to comprise, for example, an X-ray tube, an X-ray detector using the solid scintillator according to the present invention, and an image reconstruction apparatus for reconstructing an image based on data from the X-ray detector.

The tomograph according to the present invention uses a solid scintillator having short afterglow and high output for the X-ray detector and therefore provides a tomograph that can perform high speed scanning and has high output.

EXAMPLES

Examples will be shown below, but the present invention is not construed as being limited to these Examples.

Example 1

(Preparation of Reaction Promoter-Containing Powder: Reaction Promoter-Containing Powder Preparing Step)

First, using $Gd_2O_3$, $CeO_2$, $Al_2O_3$, and $Ga_2O_3$ powders as raw material powders (starting raw materials), these powders were mixed in a predetermined proportion, so that a phosphor powder after firing was a Gd garnet structure oxide of $(Gd_{0.95}Ce_{0.05})_3(Al_{0.6}Ga_{0.4})_5O_{12}$, then 500 g of a raw material mixture was obtained. $AlF_3$ was added as a reaction promoter to this raw material-mixed powder, so that the $AlF_3$ was equivalent to 200 ppm by mass of fluorine, based on a mass of the Gd garnet structure oxide $(Gd_{0.95}Ce_{0.05})_3(Al_{0.6}Ga_{0.4})_5O_{12}$ at a theoretical yield obtained by firing the raw material powders, then a reaction promoter-containing powder was prepared.

This reaction promoter-containing powder was placed in a poly bottle container containing the same volume of an ethanol solution as the reaction promoter-containing powder, and they were subjected to ball mill mixing in the poly bottle container, together with alumina balls, for 4 hours. After completion of the mixing, an obtained slurry was dried in a thermostat, and the sufficiently dried reaction promoter-containing powder was passed through a 100-mesh nylon sieve for sizing.

(Making of Phosphor Powder: Firing Step)

This sized reaction promoter-containing powder was placed in an alumina crucible, fired in air at 1250° C. for 4 hours, water-washed, dried, and sized to obtain a Gd garnet oxide phosphor powder (a powder for manufacturing a solid scintillator). The Gd garnet oxide phosphor powder has an average particle diameter $D_{50}$ of 5.0 µm and represented by $(Gd_{0.99}Ce_{0.01})_3Al_5O_{12}$ (Ce concentration: 1 mol %). This phosphor powder contained fluorine, and a fluorine content of the phosphor powder was 25 ppm by mass with respect to the Gd garnet structure oxide of the phosphor powder.

(Preparation of Mixed Powder: Mixed Powder Preparing Step)

$SiO_2$ as a sintering aid was added to the synthesized Gd garnet oxide phosphor, so that a Si equivalent amount with respect to the Gd garnet oxide phosphor was 1000 ppm, to make a mixed powder.

(Making of Sintered Body: Sintering Step)

This mixed powder was molded by a rubber press, and then, an obtained molded body was set in a carbon mold of a hot pressing (uniaxial pressing) apparatus. An Ar gas was enclosed in the hot pressing apparatus as a pressing medium, and the molded body was treated at a pressure (surface pressure) of 49 MPa and a temperature of 1700° C. for 3 hours to obtain a sintered body represented by $(Gd_{0.99}Ce_{0.01})_3Al_5O_{12}$ (Ce concentration: 1 mol %). This sintered body contained 1000 ppm of Si with respect to a mass of $(Gd_{0.99}Ce_{0.01})_3Al_5O_{12}$.

This sintered body was machined by a multi-wire saw (manufactured by Yasunaga Wire Saw Systems Co., Ltd., trade name: F-600S) to make a 25 mm long×25 mm wide×3 mm thick plate-shaped sintered body.

(Making of Scintillator: Heat Treatment Step)

Further, this plate-shaped sintered body was subjected to heat treatment in air at 1200° C. for 3 hours, using an electric furnace, to obtain a ceramic scintillator. This sample was analyzed. A fluorine content was 25 ppm by mass with respect to a Gd garnet structure oxide of the ceramic scintillator.

This ceramic scintillator radiated visible light having a peak wavelength near 550 nm when the ceramic scintillator was irradiated with X-rays at tube voltage: 120 KVp. Therefore, a linear transmittance of light having a wavelength of 550 nm was measured as an indicator of a transparency of the ceramic scintillator. Specifically, a 25 mm long×25 mm wide surface of the ceramic scintillator was irradiated with light including a wavelength of 550 nm to measure the linear transmittance (linear transmittance is hereinafter also referred to as "transmittance") of light having a wavelength of 550 nm at a thickness of 3 mm.

In addition, a light output of the ceramic scintillator was measured. Specifically, X-rays at 120 KVp were passed through a 20 mm Al filter for blocking soft X-rays, then, one 25 mm long×25 mm wide surface of the ceramic scintillator was irradiated with the X-rays, and a value of current flowing through a silicon photodiode provided on a surface on a back side of this one surface was obtained as light output. Light output was also measured for $CdWO_4$ as a comparative sample under the same conditions. The light output of the ceramic scintillator was calculated as a relative light output value (%) when the light output of $CdWO_4$ was 100%.

A composition and measurement results of the linear transmittance and relative light output value of the scintillator made are shown in Table 1 and Table 2.

TABLE 1

| | Composition of Matrix |
|---|---|
| Example 1 | $(Gd_{0.99}Ce_{0.01})_3Al_5O_{12}$(Ce: 1 mol %) |
| Example 2 | $(Gd_{0.99}Ce_{0.01})_3Al_5O_{12}$(Ce: 1 mol %) |
| Example 3 | $(Gd_{0.99}Ce_{0.01})_3Al_5O_{12}$(Ce: 1 mol %) |
| Example 4 | $(Gd_{0.99}Ce_{0.01})_3Al_5O_{12}$(Ce: 1 mol %) |
| Example 5 | $(Gd_{0.99}Ce_{0.01})_3Al_5O_{12}$(Ce: 1 mol %) |
| Example 6 | $(Gd_{0.99}Ce_{0.01})_3(Al_{0.6}Ga_{0.4})_5O_{12}$(Ce: 1 mol %) |
| Example 7 | $(Gd_{0.99}Ce_{0.01})_3(Al_{0.6}Ga_{0.4})_5O_{12}$(Ce: 1 mol %) |
| Example 8 | $(Gd_{0.99}Ce_{0.01})_3(Al_{0.6}Ga_{0.4})_5O_{12}$(Ce: 1 mol %) |
| Example 9 | $(Gd_{0.5}Tb_{0.4}Ce_{0.1})_3Al_5O_{12}$(Ce: 10 mol %) |
| Example 10 | $(Gd_{0.5}Tb_{0.4}Ce_{0.1})_3Al_5O_{12}$(Ce: 10 mol %) |
| Example 11 | $(Gd_{0.5}Tb_{0.4}Ce_{0.1})_3Al_5O_{12}$(Ce: 10 mol %) |
| Example 12 | $(Gd_{0.99}Ce_{0.01})_3(Al_{0.6}Ga_{0.4})_5O_{12}$(Ce: 1 mol %) |
| Example 13 | $(Gd_{0.5}La_{0.45}Ce_{0.05})_3(Al_{0.2}Ga_{0.8})_5O_{12}$(Ce: 5 mol %) |
| Example 14 | $(Gd_{0.95}Ce_{0.05})_3(Al_{0.6}Ga_{0.4})_5O_{12}$(Ce: 5 mol %) |
| Example 15 | $(Gd_{0.99}Ce_{0.01})Al_5O_{12}$(Ce: 1 mol %) |
| Comparative Example 1 | $(Gd_{0.99}Ce_{0.01})_3Al_5O_{12}$(Ce: 1 mol %) |
| Comparative Example 2 | $(Gd_{0.99}Ce_{0.01})_3Al_5O_{12}$(Ce: 1 mol %) |
| Comparative Example 3 | $(Gd_{0.50}La_{0.45}Ce_{0.05})_3(Al_{0.2}Ga_{0.8})_5O_{12}$(Ce: 5 mol %) |
| Comparative Example 4 | $(Gd_{0.95}Ce_{0.05})(Al_{0.6}Ga_{0.4})_5O_{12}$(Ce: 5 mol %) |

TABLE 2

| | Reaction Promoter | Amount of Fluorine in Reacton Promoter based on Oxide in Phosphor (ppm) | Content of Fluorine in Ceramic Scintillator (ppm) | Sintering Aid type | Additive Amount (ppm) | Content of Silicon in Ceramic Scintillator (ppm) | Transmittance (%) | Light Output (%) |
|---|---|---|---|---|---|---|---|---|
| Example 1 | AlF$_3$ | 200 | 25 | SiO$_2$ | 1000 | 1000 | 47 | 115 |
| Example 2 | AlF$_3$ | 200 | 25 | SiO$_2$ | 500 | 500 | 62 | 130 |
| Example 3 | AlF$_3$ | 200 | 25 | SiO$_2$ | 100 | 100 | 55 | 120 |
| Example 4 | AlF$_3$ | 200 | 25 | SiO$_2$ | 10 | 10 | 32 | 110 |
| Example 5 | AlF$_3$ | 200 | 25 | SiO$_2$ | 1 | 1 | 17 | 103 |
| Example 6 | AlF$_3$ | 200 | 25 | SiO$_2$ | 1000 | 1000 | 45 | 113 |
| Example 7 | AlF$_3$ | 200 | 25 | SiO$_2$ | 100 | 100 | 53 | 119 |
| Example 8 | AlF$_3$ | 200 | 25 | SiO$_2$ | 1 | 1 | 15 | 102 |
| Example 9 | AlF$_3$ | 200 | 25 | SiO$_2$ | 1000 | 1000 | 48 | 116 |
| Example 10 | AlF$_3$ | 200 | 25 | SiO$_2$ | 100 | 100 | 56 | 124 |
| Example 11 | AlF$_3$ | 200 | 25 | SiO$_2$ | 1 | 1 | 16 | 103 |
| Example 12 | BaF$_2$ | 400 | 40 | SiO$_2$ | 100 | 100 | 30 | 150 |
| Example 13 | BaF$_2$ | 100 | 17 | SiO$_2$ | 100 | 100 | 48 | 167 |
| Example 14 | BaF$_2$ | 10 | 4.0 | SiO$_2$ | 20 | 20 | 65 | 180 |
| Example 15 | BaF$_2$ | 400 | 40 | SiO$_2$ | 1000 | 1000 | 40 | 117 |
| Comparative Example 1 | AlF$_3$ | 200 | 25 | — | — | — | 1.0 | 43 |
| Comparative Example 2 | AlF$_3$ | 200 | 25 | SiO$_2$ | 5000 | 5000 | 2.0 | 61 |
| Comparative Example 3 | BaF$_2$ | 600 | 120 | SiO$_2$ | 100 | 100 | 11 | 80 |
| Comparative Example 4 | — | — | — | SiO$_2$ | 100 | 100 | 0.5 | 15 |

Examples 2 to 15 and Comparative Examples 1 to 4

Ceramic scintillators having compositions shown in Table 1 and Table 2 were made in the same manner as Example 1, except that raw material powders were prepared using further Tb$_4$O$_7$ and Ga$_2$O$_3$ as required.

A linear transmittance and relative light output value of the ceramic scintillators were measured in the same manner as Example 1.

A composition and measurement results of the linear transmittance and relative light output value of the scintillators made are shown in Table 1 and Table 2.

The invention claimed is:

1. A solid scintillator comprising a polycrystal, the polycrystal comprising a crystal of a Gd garnet structure oxide having a composition ratio of formula (1):

$(M_{1-x-y}Gd_xQ_y)_3J_5O_{12}$     (1),

M, where present, is at least one element selected from the group consisting of La and Tb;
Q is at least one element selected from the group consisting of Ce and Pr;
J is at least one element selected from the group consisting of Al, Ga, and In;
x and y satisfy relations $0.5 \leqq x < 1$ and $0.000001 \leqq y \leqq 0.2$;
the polycrystal further comprises 1 ppm by mass to 1000 ppm by mass of Si with respect to the Gd garnet structure oxide, and 4 ppm by mass to 87 ppm by mass of fluorine with respect to the Gd garnet structure oxide.

2. A radiation detector, comprising the solid scintillator of claim 1.

3. A tomograph, comprising the radiation detector of claim 2.

4. The solid scintillator of claim 1, wherein M is present and M of formula 1 comprises La.

5. The solid scintillator of claim 1, wherein M is present and M of formula 1 comprises Tb.

6. The solid scintillator of claim 1, wherein Q of formula 1 comprises Ce.

7. The solid scintillator of claim 1, wherein Q of formula 1 comprises Pr.

8. The solid scintillator of claim 1, wherein J of formula 1 comprises Al.

9. The solid scintillator of claim 1, wherein J of formula 1 comprises Ga.

10. The solid scintillator of claim 1, wherein J of formula 1 comprises In.

11. The solid scintillator of claim 1, wherein Q is Ce, and J is Al.

12. The solid scintillator of claim 1, wherein Q is Ce, and J is a mixture of Al and Ga.

13. The solid scintillator of claim 1,
wherein M is present,
M is Tb,
Q is Ce, and
J is Al.

14. The solid scintillator of claim 1,
wherein M is present,
M is La,
Q is Ce, and
J is a mixture of Al and Ga.

15. The solid scintillator of claim 11,
wherein M is absent,
x is 0.99, and
y is 0.01.
16. The solid scintillator of claim 12,
wherein M is absent,
x is 0.99, and
y is 0.01.
17. The solid scintillator of claim 12,
wherein M is absent,
x is 0.95, and
y is 0.05.
18. The solid scintillator of claim 13,
wherein M is present,
x is 0.5, and
y is 0.1.
19. The solid scintillator of claim 14,
wherein M is present,
x is 0.5, and
y is 0.05.
20. The solid scintillator of claim 1, wherein M is present and 1-x-y>0.

* * * * *